United States Patent
Zou et al.

(10) Patent No.: US 8,852,155 B2
(45) Date of Patent: Oct. 7, 2014

(54) MEDICINE RESERVOIR FOR DRUG DELIVERY DEVICE

(75) Inventors: Hans Zou, Windsor, NJ (US); Jeff Shimizu, Cortlandt Manor, NY (US); Lucian Remus Albu, Forest Hills, NY (US)

(73) Assignee: Medimetrics Personalized Drug Delivery, Eindhoven (NL)

( * ) Notice: Subject to any disclaimer, the term of this patent is extended or adjusted under 35 U.S.C. 154(b) by 136 days.

(21) Appl. No.: 13/390,110

(22) PCT Filed: Aug. 9, 2010

(86) PCT No.: PCT/IB2010/053580
§ 371 (c)(1),
(2), (4) Date: Feb. 7, 2013

(87) PCT Pub. No.: WO2011/018743
PCT Pub. Date: Feb. 17, 2011

(65) Prior Publication Data
US 2013/0197440 A1    Aug. 1, 2013

Related U.S. Application Data

(60) Provisional application No. 61/233,191, filed on Aug. 12, 2009.

(51) Int. Cl.
*A61M 5/178*        (2006.01)
*A61M 31/00*       (2006.01)

(52) U.S. Cl.
CPC ............. *A61M 31/00* (2013.01); *A61M 31/002* (2013.01)
USPC ...................... 604/167.02; 604/236; 604/238

(58) Field of Classification Search
USPC .............................. 604/167.02, 236, 238, 256
See application file for complete search history.

(56) References Cited

U.S. PATENT DOCUMENTS

| | | | | |
|---|---|---|---|---|
| 2,719,523 A | * | 10/1955 | Von Gierke ................... | 128/864 |
| 4,834,704 A | * | 5/1989 | Reinicke ....................... | 604/506 |
| 5,000,353 A | * | 3/1991 | Kostanecki et al. .......... | 222/207 |
| 5,947,344 A | * | 9/1999 | Jangaard ....................... | 222/494 |
| 6,142,977 A | * | 11/2000 | Kolberg et al. ............... | 604/218 |

(Continued)

FOREIGN PATENT DOCUMENTS

| | | |
|---|---|---|
| CN | 1767812 | 5/2006 |
| CN | 1774239 | 5/2006 |
| WO | WO2008059728 | 5/2008 |

OTHER PUBLICATIONS

Translated the Japanese Office Action mailed Apr. 23, 2013 for Japanese patent application No. 2012-524317, a counterpart foreign application of U.S. Appl. No. 13/390,110, 8 pages.

(Continued)

*Primary Examiner* — Nicholas Lucchesi
*Assistant Examiner* — Gerald Landry, II
(74) *Attorney, Agent, or Firm* — Lee & Hayes, PLLC

(57) ABSTRACT

A medicine reservoir (10) is provided for use with a drug delivery device (50). The medicine reservoir (10) is arranged for comprising a drug (13) and comprises a dispensing hole (15) for dispensing the drug (13) into an environment of the drug delivery device (50). The medicine reservoir (10) further comprises a deformable plug (14) which plug (14) is removable by pressure caused by a dispensing action of the drug delivery device (50).

18 Claims, 2 Drawing Sheets

(56) References Cited

U.S. PATENT DOCUMENTS

| | | | |
|---|---|---|---|
| 6,635,268 B2* | 10/2003 | Peery et al. | 424/422 |
| 7,691,626 B2* | 4/2010 | McCabe et al. | 435/307.1 |
| 7,749,191 B2* | 7/2010 | Truax | 604/90 |
| 7,766,656 B1* | 8/2010 | Feine | 433/89 |
| 7,972,339 B2* | 7/2011 | Nassiri et al. | 606/92 |
| 2003/0220585 A1* | 11/2003 | Hissong | 600/560 |
| 2004/0138611 A1* | 7/2004 | Griffiths et al. | 604/82 |
| 2004/0186432 A1* | 9/2004 | Barry et al. | 604/152 |
| 2005/0010196 A1* | 1/2005 | Fereira et al. | 604/892.1 |
| 2006/0253087 A1* | 11/2006 | Vlodaver et al. | 604/275 |
| 2007/0082398 A1* | 4/2007 | McCabe et al. | 435/373 |
| 2007/0142769 A1* | 6/2007 | Griffiths et al. | 604/82 |
| 2009/0240196 A1* | 9/2009 | Truax | 604/85 |
| 2010/0191192 A1* | 7/2010 | Prasad et al. | 604/247 |

OTHER PUBLICATIONS

Translated the Chinese Office Action mailed Oct. 12, 2013 for Chinese patent application No. 201080046012.8, a counterpart foreign application of U.S. Appl. No. 13/390,110, 14 pages.

* cited by examiner

MEDICINE RESERVOIR FOR DRUG DELIVERY DEVICE

FIELD OF THE INVENTION

This invention relates to a medicine reservoir for use with a drug delivery device, the medicine reservoir being arranged for comprising a drug and comprising a dispensing hole for dispensing the drug into an environment of the drug delivery device.

This invention further relates to a drug delivery device comprising such a medicine reservoir.

BACKGROUND OF THE INVENTION

Such drug delivery devices make it possible to control the release of drugs in the gastrointestinal tract. The drug delivery may take place in accordance with a predetermined delivery schedule and/or may be triggered by external signals or environmental conditions. The device may include additional electronics, sensors and communication devices for controlling the drug delivery. In many swallowable drug delivery devices, the drug release is effected using a displacement based actuator system. For example, a piston may push a predetermined amount of the drug through the dispensing hole.

The dispensing hole often is an open orifice. However, an open orifice introduces the possibility for exchange of material between the reservoir and outside environment, resulting, for example, in delivery of the drug before the intended time and a reduction of the amount delivered when intended. The main processes involved are diffusion and convection. Diffusion, because of the open connection between the inside and the outside of the capsule. Convection, because of small differences in specific weight of the substance stored in the capsule and the fluid outside. E.g. when the fluid in the capsule is heavier than the fluid in the intestines and the hole is directed downwards the fluid in the capsule flows out and will be replaced by the fluid of the intestines. Both processes may be slowed down by reduction in the exit hole cross-sectional size, extending the length of the exit hole and increasing the viscosity of the material in the reservoir. However the hole dimensions and the viscosity of the medicine to be administered must be chosen such that it allows the actuator to dispense the medicine.

Often, a valve is used for separating the drug reservoir from the outside environment. Valves which operate in small spaces, provide good sealing and use low power are however very difficult to implement. It would thus be advantageous to avoid diffusion or convection of the drug without the use of a valve.

OBJECT OF THE INVENTION

It is an object of the invention to provide a medicine reservoir for a drug delivery device according to the opening paragraph, which device does not need a valve for keeping the drug inside until the intended moment of release.

SUMMARY OF THE INVENTION

According to a first aspect of the invention, this object is achieved by providing a medicine reservoir for use with a drug delivery device, the medicine reservoir being arranged for comprising a drug and comprising a dispensing hole for dispensing the drug into an environment of the drug delivery device, the medicine reservoir further comprising a deformable plug which plug is removable by a pressure caused by a dispensing action of the drug delivery device.

As long as no drug is delivered, the plug seals the dispensing hole and no drug is allowed to leave the medicine reservoir. When the drug delivery device tries to deliver a first amount of the drug, the pressure inside the medicine reservoir increases. The resulting pressure upon the plug then causes the plug to be pushed out of the dispensing hole, thereby enabling the delivery of the drug to the environment. The composition and dimensions of the deformable plug are such that the plug is easily removed by the pressure caused by the first drug delivery. Concurrently, the composition and dimensions of the plug should ensure that the plug will not be removed due to other causes (e.g. temperature changes, gravity, diffusion). A non-deformable plug such as, e.g., a plastic plug would be very suitable for sealing the dispensing hole, but cannot be removed by the dispensing action of the drug delivery device. For easy removal, the plug should be deformable.

A suitable plug may, for example, comprise an oil which does not mix with the drug or the gastro-intestinal fluid. For example, a mineral oil or castor oil is very suitable for use as a plug in a medicine reservoir according to the invention, but other non-rigid materials may also be used. When the plug material does not mix with the drug or the medium outside the drug delivery device, the plug will not disintegrate before the first drug delivery is due. In most drug delivery devices oily materials are very suitable because they do not mix with the watery gastro-intestinal environment or the drugs which are often supplied in a watery solution.

In a preferred embodiment of the medicine reservoir according to the invention, a nozzle is provided for partly filling the dispensing hole, the nozzle comprising the deformable plug. The main advantage of the use of the nozzle is that the same drug delivery device and medicine reservoir may be used for different drugs. Due to differences in, e.g., viscosity, different drugs may require dispensing holes with different dimensions (length and/or diameter). Different nozzles may be designed for different drugs, such that a dispensing hole with optimal dimensions is available for all drug types. The holes in those nozzles are filled with the plug according to the invention. The filled nozzle is then used for sealing the medicine reservoir. When the first amount of drug is to be delivered and the pressure inside the medicine reservoir increases, the plug will be pushed out of the nozzle. The resulting dispensing hole will then have the desired dimensions.

These and other aspects of the invention are apparent from and will be elucidated with reference to the embodiments described hereinafter.

DETAILED DESCRIPTION OF THE INVENTION

Figure 1:
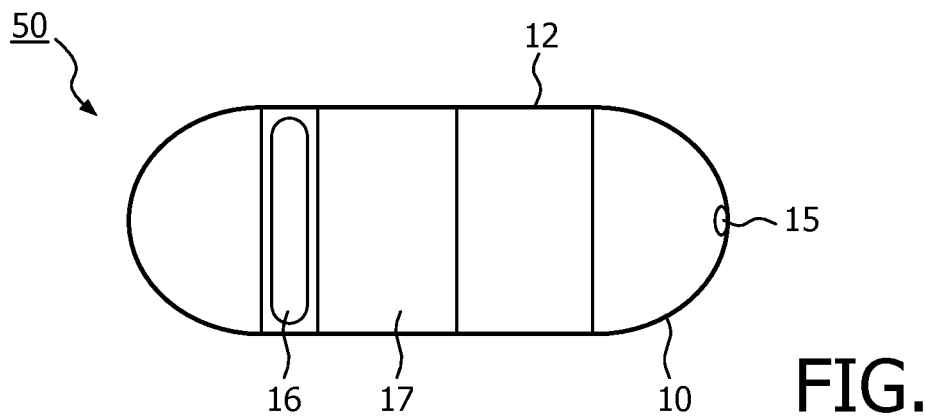
FIG. 1 schematically shows a drug delivery device with a medicine reservoir according to the invention, FIG. 2 schematically shows a medicine reservoir according to the invention.

FIG. 1 schematically shows a drug delivery device 50 with a medicine reservoir according to the invention. The drug delivery device 50 is a swallowable capsule comprising a drug to be released somewhere along the gastro-intestinal tract of a patient and an actuation mechanism for controlling the amount of drugs to be released and the moment of said release. Although the deformable and removable plug according to the invention is particularly advantageous in combination with swallowable drug delivery devices 50, it is to be noted that it may also be used with implantable drug delivery devices. The drug to be released is stored in a compressible medicine reservoir 10. The drug may, e.g., be stored as dry powder, dissolved in water or as a gel or liquid. An actuator means 12 is provided for compressing the medicine reservoir 10, resulting in an increase of the pressure inside the medicine reservoir 10. Instead of a compressible medicine reservoir 10, a rigid reservoir may be used comprising a substance or element which is capable of increasing the pressure inside the reservoir. For example, a balloon filled with a swelling agent may be placed in the rigid reservoir.

The medicine reservoir comprises a dispensing hole 15 for allowing the drug to be pushed out of the drug delivery device 50 when the pressure inside the medicine reservoir 10 increases. The actuator means 12 may work mechanically using, e.g., a piston. Alternatively, the actuator means 12 may increase the pressure by sucking in water from the environment or by using chemical reactions for producing water or for expanding a volume of a swelling agent. The drug release may, e.g., be triggered by an internal clock, sensor values from a pH-sensor or trigger signals from an electrical or chemical detector element. If the drug delivery device 50 comprises means for wireless communication, the drug delivery may be externally triggered. The operation of all electronic functions of the device 50 is controlled by the processing electronics 17 and powered by a battery 16.

Figure 2:
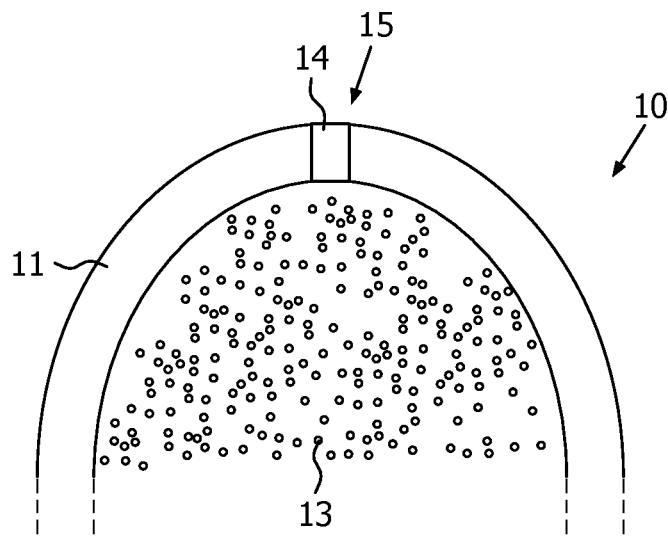

FIG. 2 schematically shows (part of) a medicine reservoir 10 according to the invention. The medicine reservoir 10 is filled with a drug 13 and is partially enclosed by a housing 11 of the drug delivery device 50. Here, the housing 11 of the drug delivery device 50 is also a wall of the medicine reservoir 10. Alternatively, the medicine reservoir 10 may be a small bag inside the housing 11. The medicine reservoir 10 is separated from the external environment of the drug delivery device 50 by a dispensing hole 15 in the housing 11 of the device. In this Figure, the dispensing hole 15 is blocked by a deformable plug 14. The plug 14 prevents the drug 13 from leaking out of the medicine reservoir 10.

The plug 14 may comprise an oil which does not mix with the drug 13 or the gastro-intestinal fluid outside the drug delivery device 50. For example, a mineral oil or castor oil is very suitable for use as a plug 14. Other non-rigid deformable materials may also be used. When the actuator means 12 of the drug delivery device 50 raise the pressure inside the medicine reservoir 10, the deformable plug 14 will first be compressed and will then be pushed out of the dispensing hole 15, followed by the first amount of drugs 13 to be released.

Figure 3:
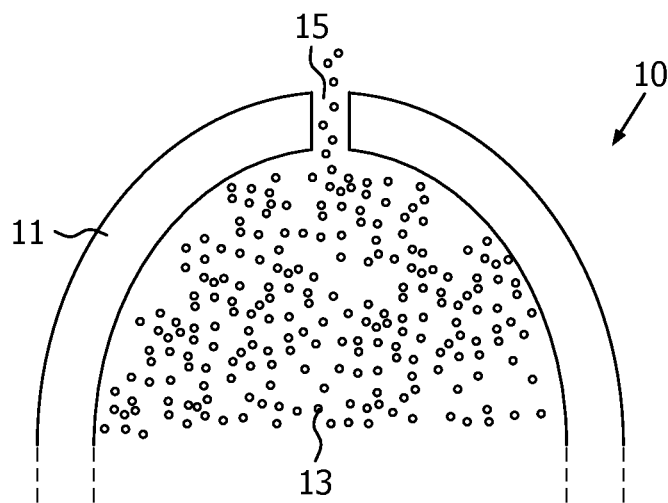
FIG. 3 shows the medicine reservoir of FIG. 2 with the plug removed.

FIG. 3 shows the medicine reservoir of FIG. 2 with the plug removed. When the actuator means 12 compress the medicine reservoir 10, drugs 13 are pushed out through the dispensing hole 15.

Figure 4:
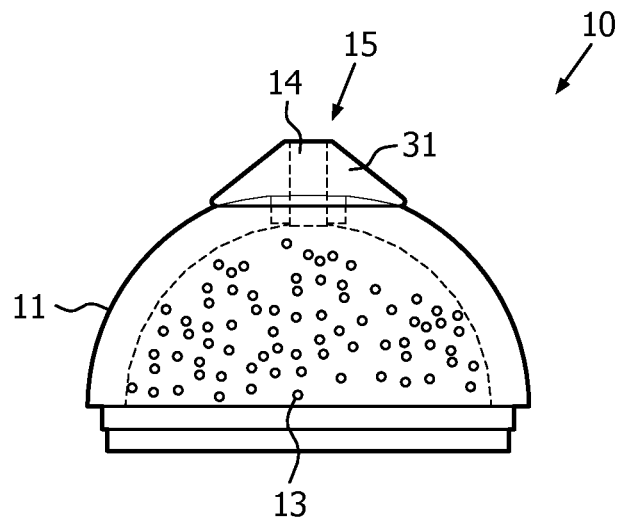
FIG. 4 shows a medicine reservoir with a nozzle comprising a plug.
Figure 5:
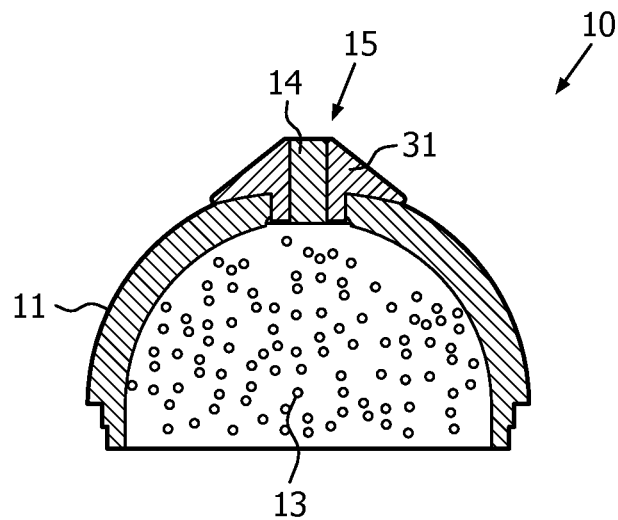
FIG. 5 shows a cross section of the medicine reservoir of FIG. 4.

FIG. 4 shows a medicine reservoir 10 with a nozzle 31 comprising a plug 14. FIG. 5 shows a cross section of the medicine reservoir of FIG. 4. The main advantage of the use of the nozzle 31 is that the same drug delivery device 50 and medicine reservoir 10 may be used for different drugs 13. Due to differences in, e.g., viscosity, different drugs 13 may require dispensing holes 15 with different dimensions (length and/or diameter). Different nozzles 31 may be designed for different drugs 13, such that a dispensing hole 15 with optimal dimensions is available for all drug types. A thick gel does, for example, require a relatively wide dispensing hole 15, while more liquid drugs require very narrow dispensing holes 15. The hole 15 in the nozzle 31 is filled with a plug 14 as described above. The filled nozzle 31 seals the medicine reservoir 10. When the first amount of drug 13 is to be delivered and the pressure inside the medicine reservoir 10 increases, the plug 14 is pushed out of the nozzle 31. The dimensions of the dispensing hole 15 are defined by the design of the nozzle 31.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A medicine reservoir for use with a drug delivery device, the medicine reservoir being arranged for comprising a drug and comprising:
   a dispensing hole for dispensing the drug into an environment of the drug delivery device; and
   a deformable oil plug that does not mix with the drug or with gastro-intestinal fluid disposed in and sealing the dispensing hole, wherein the plug is ejected from the dispensing hole in response to a pressure in the reservoir caused by a dispensing action of the drug delivery device.

2. A medicine reservoir as claimed in claim 1, wherein the oil plug comprises a mineral oil.

3. A medicine reservoir as claimed in claim 1, wherein the oil comprises castor oil.

4. A medicine reservoir as claimed in claim 1, further comprising a nozzle for partly filling the dispensing hole, the nozzle comprising the deformable plug.

5. A drug delivery device comprising a medicine reservoir as claimed in claim 1.

6. A drug delivery device as claimed in claim 5, further comprising electronics for controlling the dispensing action.

7. A drug delivery device comprising:
   a housing with a dispensing hole formed therein;
   a medicine reservoir disposed in the housing and defining a volume in fluid communication with the dispensing hole;
   an actuator disposed to increase a pressure in the volume to dispense a medicine contained in the medicine reservoir through the dispensing hole; and
   a deformable oil plug disposed in the dispensing hole.

8. The drug delivery device of claim 7, further comprising a nozzle disposed in the dispensing hole and having a nozzle hole therethrough, and wherein the deformable plug is disposed in the nozzle hole.

9. The drug delivery device of claim 7, wherein the oil plug comprises castor oil or mineral oil.

10. The drug delivery device of claim 7, wherein the oil does not mix with the medicine or gastrointestinal fluid.

11. The drug delivery device of claim 7, wherein an inner wall of the housing forms a portion of the reservoir.

12. The drug delivery device of claim 7, further comprising processing electronics disposed in the housing for controlling the actuator.

13. The drug delivery device of claim 7, wherein the actuator is a mechanical actuator.

14. The drug delivery device of claim 7, wherein the actuator utilizes a chemical reaction.

15. The drug delivery device of claim 7, wherein the increase in the pressure in the volume acts to eject the plug from the dispensing hole.

16. A drug delivery device comprising:
a housing with a dispensing hole formed therein;
a medicine reservoir disposed in the housing and defining a volume in fluid communication with the dispensing hole;
a nozzle disposed in the dispensing hole and having a nozzle hole formed therethrough; and an oil plug disposed in the nozzle hole.

17. The drug delivery device of claim 16, wherein the oil plug comprises castor oil or mineral oil.

18. The drug delivery device of claim 16, wherein the nozzle hole has a diameter chosen based on a viscosity of a drug to be delivered by the drug delivery device.

* * * * *